(12) United States Patent
Rohera (10) Patent No.: US 12,226,183 B2
(45) Date of Patent: Feb. 18, 2025

(54) MEDICAL THERAPEUTIC DEVICE

(71) Applicant: Hemant Karamchand Rohera, Pune-Maharashtra (IN)

(72) Inventor: Hemant Karamchand Rohera, Pune-Maharashtra (IN)

( * ) Notice: Subject to any disclaimer, the term of this patent is extended or adjusted under 35 U.S.C. 154(b) by 334 days.

(21) Appl. No.: 17/753,643

(22) PCT Filed: Jun. 5, 2020

(86) PCT No.: PCT/IB2020/055292
§ 371 (c)(1),
(2) Date: Mar. 10, 2022

(87) PCT Pub. No.: WO2021/048642
PCT Pub. Date: Mar. 18, 2021

(65) Prior Publication Data
US 2022/0330821 A1 Oct. 20, 2022

(30) Foreign Application Priority Data
Sep. 10, 2019 (IN) .............................. 201921036412

(51) Int. Cl.
*A61B 5/00* (2006.01)
*A61B 5/0205* (2006.01)

(52) U.S. Cl.
CPC ............ *A61B 5/002* (2013.01); *A61B 5/0004* (2013.01); *A61B 5/0024* (2013.01);
(Continued)

(58) Field of Classification Search
CPC ..... A61B 5/002; A61B 5/0004; A61B 5/0024; A61B 5/02055; A61B 5/6813; A61B 5/74;
(Continued)

(56) References Cited

U.S. PATENT DOCUMENTS

2016/0213924 A1\* 7/2016 Coleman .............. A61N 1/0484
2016/0263318 A1 9/2016 Osorio
(Continued)

FOREIGN PATENT DOCUMENTS

CN 206081033 U \* 4/2017
WO WO-2012048302 A2 \* 4/2012 ........... A61B 5/0002
WO 2017125798 A1 7/2017

*Primary Examiner* — Jonathan T Kuo
(74) *Attorney, Agent, or Firm* — John A. Miller; Shumaker, Loop & Kendrick, LLP (57) ABSTRACT

The present disclosure relates to the field of medicine and discloses a medical therapeutic device for monitoring and treating medical condition of patients. The device comprises an input unit, a plurality of sensors, a control unit, a waveform generator unit, and a coupling means. The input unit receives at least one input from a user. The sensors monitor a plurality of predetermined parameters associated with the health of a patient generate detection signals based on the monitored parameters. The control unit selects a program based on the input and the detection signals. The waveform generator unit generates a therapeutic signal of pre-determined values of at least one of voltage, current, and frequency based on the selected program for facilitating treatment of medical condition corresponding to the selected program.

20 Claims, 3 Drawing Sheets

(52) U.S. Cl.
CPC ........ *A61B 5/02055* (2013.01); *A61B 5/6813* (2013.01); *A61B 5/74* (2013.01)

(58) Field of Classification Search
CPC ................ A61B 5/0205; A61B 5/4839; A61B 2562/0247; A61B 2562/0271; A61B 5/02416; A61B 5/1107; A61B 5/28; A61B 5/291; A61B 5/296; A61B 5/297; A61B 5/4836; A61B 5/6802; A61B 5/01; A61B 5/11; A61B 5/145; A61B 5/165; A61B 5/4806; A61H 2201/0157; A61H 2201/0207; A61H 2201/10; A61H 2201/1207; A61H 2201/165; A61H 2201/501; A61H 2201/5023; A61H 2201/5046; A61H 2201/5097; A61H 2230/045; A61H 2230/065; A61H 2230/085; A61H 2230/206; A61H 2230/208; A61H 2230/305; A61H 2230/505; A61H 2230/605; A61H 23/02; A61H 39/002; A61N 1/36014; A61N 2/008; A61N 2/02; A61N 1/36031; A61N 1/025; A61N 1/0456; A61N 1/323; A61N 1/36017; A61N 1/36034; A61N 1/39; G16H 40/67; G16H 50/30; G16H 20/00; G16H 80/00; G16H 20/30; A61F 7/08; A61M 21/00; A61M 2205/3584; A61M 2205/505; A61M 2205/8206

See application file for complete search history.

(56) References Cited

U.S. PATENT DOCUMENTS

2016/0339261 A1* 11/2016 Mletzko .................... H05H 1/46
2019/0335551 A1* 10/2019 Williams ............... H05B 45/24

* cited by examiner

MEDICAL THERAPEUTIC DEVICE

CROSS-REFERENCE TO RELATED APPLICATIONS

This application is a National Stage application of International Application No. PCT/IB2020/055292 filed on Jun. 5, 2020, which claims priority to India Application No. 201921036412 filed Sep. 10, 2019.

BACKGROUND

Field

The present disclosure generally relates to the field of medical devices, and specifically, to a medical therapeutic device for monitoring and treating medical conditions of patients.

Discussion of the Related Art

As used in the present disclosure, the following terms are generally intended to have the meaning as set forth below, except to the extent that the context in which they are used indicate otherwise.

Electrocardiogram (ECG)—The expression "electrocardiogram" or "ECG" hereinafter refers to a diagnostic tool that is used to assess the electrical and muscular functions of the heart to know whether or not it is working normally.

Photoplethysmogram (PPG)—The expression "photoplethysmogram" or "PPG" hereinafter refers to a simple optical technique that is used to detect volumetric changes in blood in peripheral circulation.

SpO2—The expression "SpO2" stands for peripheral capillary oxygen saturation and hereinafter refers to an estimate of the amount of oxygen in the blood. More specifically, it is the percentage of oxygenated haemoglobin compared to the total amount of haemoglobin in the blood (oxygenated and non-oxygenated haemoglobin).

Defibrillation—The expression "defibrillation" hereinafter refers to a technique used in emergency medicine to stop fibrillation of the heart by administering a controlled electric shock, to allow restoration of the normal rhythm.

Transcutaneous Electrical Nerve Stimulation/TENS/Electrical muscle stimulation—The expressions "Transcutaneous Electrical Nerve Stimulation", "TENS", and Electrical muscle stimulation hereinafter refer to a treatment which involves administering small electrical impulses through electrodes attached to a person's skin to stimulate the nerves for therapeutic purposes.

Interferential Therapy (IFT)—The expression "Interferential Therapy" or "IFT" hereinafter refers to a type of electrotherapy treatment that uses electric currents to stimulate tissues for providing pain relief, reduction in swelling and many other health benefits.

Electromyography (EMG)—The expression "Electromyography" or "EMG" hereinafter refers to a diagnostic medicine technique for evaluating and recording the electrical activity produced by skeletal muscles.

Electro-acupuncture—The expression "electro-acupuncture" hereinafter refers to a form of acupuncture where a small electric current is passed between pairs of acupuncture needles that are inserted on specific points along the body to treat pain and restore health and well-being.

User—The expression "user" hereinafter refers to a person who operates the medical therapeutic device of the present disclosure. The user can be a patient, patient's caretaker, a physician, or a doctor.

The background information herein below relates to the present disclosure but is not necessarily prior art.

Currently, a wide variety of therapeutic devices are used in medical applications. These therapeutic devices mainly make use of electrical fields, electromagnetic fields, and magnetic fields to treat specific illnesses and disorders. A magnetic field is a magnetic force that extends out from a magnet. An electromagnetic field is produced by passing electric currents through coils. When an alternating current is passed through a coil, a dynamic magnetic field is produced. The strength of the magnetic field is proportional to the current passed. An electromagnetic filed refers to the dynamic magnetic field which contains both an electric and a magnetic field. An important parameter used to characterize an electromagnetic wave is the rate or frequency of electromagnetic energy, which refers to the number of fluctuations and is expressed in hertz or cycles per second.

These therapeutic devices typically consist of electrodes to radiate electrical and electromagnetic waves. The patient's body parts are exposed to these radiations to provide rapid healing. It is generally known that electrical and electromagnetic waves can produce favorable biological effects. For example, electrotherapy which involves application of electrical waves to the human body is used for relaxation of muscle spasms, muscle rehabilitation and re-education electrical muscle stimulation, prevention and retardation of disuse atrophy, increase of local blood circulation, maintaining and increasing range of motion, management of chronic and intractable pain, post-surgical acute pain, post-traumatic acute pain, immediate post-surgical stimulation of muscles to prevent venous thrombosis, wound healing and drug delivery. Similarly, electromagnetic therapy makes use of electromagnetic waves for bone healing, post-surgical pain and healing, inflammation healing, knee pain and even depression.

The conventional therapeutic devices allow selection of the duration of treatment and the frequency as well as automatic programs suitable to perform cycles of predetermined frequencies applications for a certain predetermined time. Some of the therapeutic devices also allow selection of specific positive voltage for treatment of certain illnesses and disorders. However, these devices often require the presence of an operator who must position the electrodes on the patient's body, as well as supervise control and command of the device itself. Further, conventional therapeutic devices are not capable of integrating various therapeutic techniques so as to provide healing and treatment for a wide range of blood-related illnesses and disorders such as leukemia, lymphoma, diabetes, glaucoma, high blood pressure, and hemophilia. The prevailing therapeutic devices also do not facilitate real-time remote monitoring of various health parameters of a patient's body, leaving no means to facilitate patients to access emergency healthcare.

There is, therefore, felt a need to provide a therapeutic device that eliminates the above-mentioned drawbacks.

SUMMARY

Some of the objects of the present disclosure, which at least one embodiment herein satisfies, are as follows:

It is an object of the present disclosure to ameliorate one or more problems of the prior art or to at least provide a useful alternative.

It is an object of the present disclosure to provide a medical therapeutic device.

Another object of the present disclosure is to provide a medical therapeutic device that facilitates real-time monitoring of various health parameters of a patient's body.

Still another object of the present disclosure is to provide a medical therapeutic device that is capable of treating multiple illnesses and disorders.

Yet another object of the present disclosure is to provide a medical therapeutic device that restores the zeta potential of the body cell.

Still another object of the present disclosure is to provide a medical therapeutic device that facilitates remote monitoring of the patient's health.

Yet another object of the present disclosure is to provide a medical therapeutic device that can be integrated with a hospital's health record system.

Still another object of the present disclosure is to provide a medical therapeutic device that is wearable.

Yet another object of the present disclosure is to provide a medical therapeutic device that notifies a physician, a registered hospital, or a caretaker about a medical emergency situation.

Still another object of the present disclosure is to provide a medical therapeutic device that enables a patient to access emergency healthcare.

Yet another object of the present disclosure is to provide a medical therapeutic device that is capable of treating blood-related illnesses and disorders.

Other objects and advantages of the present disclosure will be more apparent from the following description, which is not intended to limit the scope of the present disclosure.

The present disclosure envisages a therapeutic device for monitoring and treating medical conditions of patients. The device comprises an input unit, a plurality of sensors, a control unit, a waveform generator unit, and a coupling means. The input unit is configured to receive at least one input from a user. The input unit includes at least one of a keypad, a touch screen, push buttons, and toggle switches. Each of the sensors is configured to monitor a plurality of pre-determined parameters associated with the health of the patient. The sensors are further configured to generate detection signals based on the monitored parameters. The sensors include at least one of an Electrocardiogram (ECG) sensor, a photoplethysmogram (PPG) sensor, an electroretinogram (ERG) sensor, a myogram sensor, a blood pressure sensor, a glucometer, a temperature sensor, an oxygen saturation sensor (SpO2 sensor), a heart rate sensor, an Invasive (intra-arterial) blood pressure (IBP) sensor, a heart chamber pressure sensor, a neuromuscular monitoring device, an End-Tidal CO2 sensor (EtCO2 sensor), a pulse oximeter, and a fitness tracker for tracking stress, heart rate variability (HRV), sleep data, steps, calories burnt, cumulative distance walked, and heart activity data of the patient. Accordingly, the monitored parameters include heart rate, pulse rate, ECG, PPG, Blood Pressure (BP), oxygen saturation (SpO2), level of carbon dioxide released at the end of expiration, respiration rate, neuromuscular blockade, blood glucose level, skin temperature, calories burnt, stress level, cumulative distance walked, and duration of sleep. The control unit is configured to cooperate with the input unit and the sensors. The control unit comprises a memory and a controller. The memory includes a list of medical conditions to be treated and a program corresponding to each of the medical conditions. Each of the programs comprises pre-determined values of at least one of voltage, current, and frequency required for treating corresponding medical condition. The pre-determined values of voltage include positive as well as negative voltage values. The controller is configured to receive the input from the input unit and the detection signals from the sensors. The controller is further configured to cooperate with the memory to select a program based on the received input, the detection signals, or combination thereof. The waveform generator unit is configured to cooperate with the control unit to receive the selected program, and is further configured to generate a therapeutic signal of the pre-determined values of at least one of voltage, current, and frequency associated with the selected. The coupling means enables mounting of the waveform generator unit proximity to the patient's body for injecting the therapeutic signal into the patient's body to facilitate treatment of medical condition corresponding to the selected program.

In an embodiment, the waveform generator unit is implemented using a microcontroller. In an embodiment, the therapeutic signal comprises a series of pulses.

In an embodiment, the therapeutic signal is an electromagnetic signal. The waveform generator unit includes a plurality of treatment coils, a first signal generator unit, and a coil driver circuit. The first signal generator unit is configured to generate a drive signal of the pre-determined values of at least one of voltage, current, and frequency associated with the selected program. The coil driver circuit is configured to cooperate with the first signal generator unit to receive the generated drive signal, and is further configured to condition the received drive signal based on the requirement and number of the treatment coils. The coil driver circuit is configured to provide the conditioned drive signal to the treatment coils for facilitating generation of the electromagnetic signal. The treatment coils generate the electromagnetic signal to facilitate treatment of medical condition corresponding to the selected program. In an embodiment, the treatment coils are electromagnetic coils. In one embodiment, the waveform generator unit generates the electromagnetic signal for facilitating treatment of medical conditions by improving the zeta potential of cells in the body of the patient.

In another embodiment, the therapeutic signal is an electrical signal. The waveform generator unit includes a second signal generator unit configured to generate the electrical signal of the pre-determined values of at least one of voltage, current, and frequency associated with the selected program for facilitating treatment of medical condition corresponding to the selected program. In an embodiment, the second signal generator unit is connectable to red, near-infrared, and infrared Light Emitting Diodes (LEDs) to enable generation of red, near-infrared, and infrared light beams for facilitating treatment of medical conditions. In another embodiment, the second signal generator unit is connectable to a current control unit to provide electrical stimulation therapies including at least one of facial stimulation, pelvic stimulation, Transcutaneous Electrical Nerve Stimulation (TENS), Interferential Therapy (IFT), Defibrillation, and electro-acupuncture for facilitating treatment of medical conditions. In still another embodiment, the device is connectable to a thermal pad for facilitating healing of the patient by using thermotherapy. In an alternate embodiment, the device includes at least one of an HDMI interface and a USB interface for storing a plurality of music notes to facilitate healing of the patient with the help of music therapy.

In an embodiment, the device is embedded with a wireless communication module selected from a group consisting of 2G (GSM), 3G (GPRS), 4G (LTE), narrowband IoT (NB-IoT/5G), Zigbee modules for facilitating wireless communication with a remote cloud server. The device facilitates real-time monitoring of the parameters remotely via a monitoring device communicatively coupled to the remote cloud server.

In one embodiment, the device includes a health evaluation unit comprising a signal conditioning unit and a comparator. The signal conditioning unit is configured to cooperate with the sensors to receive the detection signals, and is further configured to generate detection values based on the detection signals. The comparator is configured to cooperate with the signal conditioning unit to receive the detection values, and is further configured to compare each of the received detection values with at least one pre-determined threshold value to evaluate the health condition of the patient. The comparator is configured to generate an alert signal when the detection values become equal to the pre-determined threshold values. In an embodiment, the health evaluation unit is configured to send the generated alert signal to the monitoring device via the remote cloud server.

In an embodiment, the device facilitates provision of the inputs remotely through the monitoring device via the remote cloud server.

In an embodiment, the coupling means is made of a conducting material. In another embodiment, the coupling means is selected from a group consisting of a belt, a contact surface, a set of probes, cables, and a set of electrodes.

Advantageously, the device is integrated with a hospital's health record system via the remote cloud server.

Advantageously, the device is a portable and wearable device.

BRIEF DESCRIPTION OF THE DRAWINGS

A medical therapeutic device of the present disclosure will now be described with the help of the accompanying drawing, in which.

The following is a list of reference numerals that are used in the figures.

100— Device
102— Input unit
104*a-n*—Sensors
106—Control unit
108—Memory
110—Controller
112—Waveform generator unit
114—Power source
116—Health evaluation unit
118—Signal conditioning unit
120—Comparator
202—First signal generator unit
204—Coil driver circuit
206*a-s*—Treatment coils
300—Monitoring device
302—Remote cloud server

DETAILED DESCRIPTION OF THE EMBODIMENTS

Embodiments, of the present disclosure, will now be described with reference to the accompanying drawing.

Embodiments are provided so as to thoroughly and fully convey the scope of the present disclosure to the person skilled in the art. Numerous details, are set forth, relating to specific components, and methods, to provide a complete understanding of embodiments of the present disclosure. It will be apparent to the person skilled in the art that the details provided in the embodiments should not be construed to limit the scope of the present disclosure. In some embodiments, well-known processes, well-known apparatus structures, and well-known techniques are not described in detail.

The terminology used, in the present disclosure, is only for the purpose of explaining a particular embodiment and such terminology shall not be considered to limit the scope of the present disclosure. As used in the present disclosure, the forms "a," "an," and "the" may be intended to include the plural forms as well, unless the context clearly suggests otherwise. The terms "comprises," "comprising," "including," and "having," are open ended transitional phrases and therefore specify the presence of stated features, integers, operations, elements, modules, units and/or components, but do not forbid the presence or addition of one or more other features, integers, operations, elements, components, and/or groups thereof.

As used herein, the term "and/or" includes any and all combinations of one or more of the associated listed elements.

Figure 2:
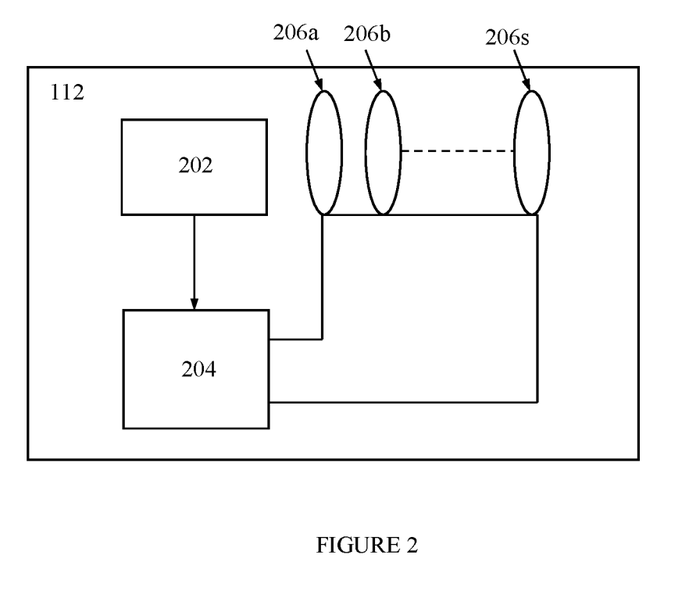
FIG. 2 illustrates a block diagram of a waveform generator unit of the device of FIG. 1, in accordance with an embodiment of the present disclosure.
Figure 3:
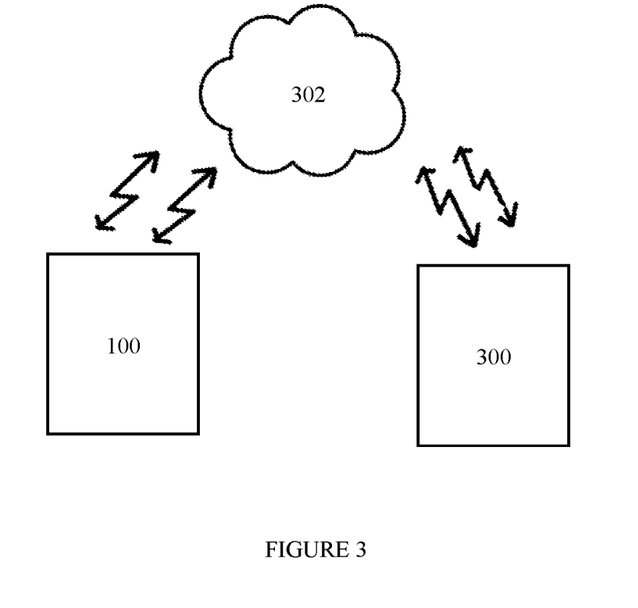
FIG. 3 illustrates a block diagram depicting connection of a remote monitoring device with the device of the FIG. 1 via a remote cloud server.

A medical therapeutic device (hereinafter referred as "device 100"), of the present disclosure, is now being described with reference to FIG. 1 through FIG. 3. Unlike conventional therapeutic devices, the device 100 of the present disclosure is a unique, state of the art, smart, drug-free, micro-medical therapeutic device that brings multiple alternative therapies on a single platform to treat illnesses and disorders. The device 100 is also capable of facilitating real-time monitoring of health of the patients. The device 100 is available in wearable, portable form and can be customized as big as a hospital bed.

Figure 1:
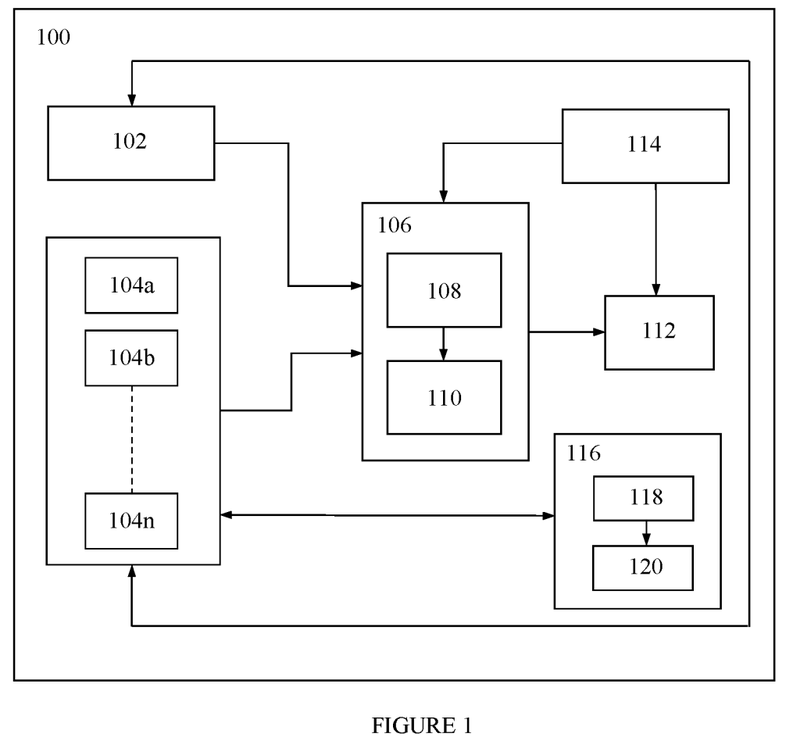
FIG. 1 illustrates a block diagram of a medical therapeutic device of the present disclosure.

Referring to FIG. 1, the therapeutic device 100 comprises an input unit 102, a plurality of sensors 104*a-n*, a control unit 106, a waveform generator unit 112, and a coupling means (not shown in figures). The input unit 102 is configured to receive at least one input from a user. Each of the sensors 104*a-n* is configured to monitor a plurality of pre-determined parameters associated with the health of a patient. The sensors 104*a-n* are further configured to generate detection signals based on the monitored parameters. The sensors 104*a-n* include at least one of an Electrocardiogram (ECG) sensor, a photoplethysmogram (PPG) sensor, an electroretinogram (ERG) sensor, a myogram sensor, a blood pressure sensor, a glucometer, a temperature sensor, an oxygen saturation sensor (SpO2 sensor), a heart rate sensor, an Invasive (intra-arterial) blood pressure (IBP) sensor, a heart chamber pressure sensor, a neuromuscular monitoring device, an End-Tidal CO2 sensor (EtCO2 sensor), a pulse oximeter, and a fitness tracker for tracking stress, heart rate variability (HRV), sleep data, steps, calories burnt, cumulative distance walked, and heart activity data of the patient. In an embodiment, the sensors 104*a-n* are fitted within the device 100. In an embodiment, a plurality of sensors may be integrated to form a single unit. The device 100 may include multiple such integrated units, wherein each integrated unit may be configured to monitor multiple health parameters. In another embodiment, the sensors may be connected externally to the device. For example, the glucometer is a continuous analyte monitor and may include a sensor that is placed subcutaneously, transdermally (e.g., transcutaneously), or intravascularly. The monitored parameters of the plurality of sensors include heart rate, pulse rate, ECG, PPG, Blood Pressure (BP), oxygen saturation (SpO2), level of carbon dioxide released at the end of expiration, respiration rate, neuromuscular blockade, blood glucose level, skin temperature, calories burnt, stress level, cumulative distance walked, and duration of sleep. The monitored parameters may be converted into values and displayed on a display screen of the device 100.

The control unit 106 is configured to cooperate with the input unit 102 and the sensors 104a-n. The control unit 106 comprises a memory 108 and a controller 110. The memory 108 includes a list of medical conditions to be treated and a program corresponding to each of the medical conditions. Each of the programs comprises pre-determined values of at least one of voltage, current, and frequencies required for treating corresponding medical condition. The pre-determined voltage values include positive as well negative voltage values. The memory 108 may be configured to store the list of medical conditions and corresponding programs in the form of one or more lookup tables. The controller 110 is configured to receive the input from the input unit 102 and the detection signals from the sensors 104a-n. The controller 110 is further configured to cooperate with the memory 108 to select a program based on the received input, the detection signals, or combination thereof. The waveform generator unit 112 is configured to cooperate with the control unit 106 to receive the selected program, and is further configured to generate a therapeutic signal of the pre-determined values of at least one of voltage, current, and frequency associated with the selected program. Thus, upon selecting the program, the device 100 executes the program by generating a therapeutic signal having a voltage, current, and/or frequency corresponding to the selected program for treating the patient. In an embodiment, the memory 108 also stores a pre-defined time duration for each of the programs. The device 100 allows selection of an automatic program to perform cycles of a predetermined voltage, current, and/or frequency for the associated pre-defined time duration. In an embodiment, the default pre-defined time duration is 30 minutes for each program. The coupling means enables mounting of the waveform generator unit 112 proximity to the patient's body for injecting said therapeutic signal into the patient's body to facilitate treatment of medical condition corresponding to the selected program. In an embodiment, the coupling means is made of a conducting material. In another embodiment, thee coupling means is selected from a group consisting of a belt, a contact surface, a set of probes, cables, a set of electrodes, and the like. In an embodiment, the sensors 104a-n may be coupled to the patient's body by means of cables, probes, or electrodes. When the sensors are not in use, the coupling means of the sensors 104a-n can be utilized for injecting the therapeutic signals into the patient's body.

In an embodiment, the waveform generator unit 112 is implemented using a microcontroller. In an embodiment, the therapeutic signal is a pulsed signal.

In an embodiment, the therapeutic signal is an electromagnetic signal. The waveform generator unit 112 includes a plurality of treatment coils 206a-s, a first signal generator unit 202, and a coil driver circuit 204. The first signal generator unit 202 is configured to generate a drive signal of the pre-determined values of at least one of voltage, current, and frequency associated with the selected program. The first signal generator unit 202 is capable of generating drive signals of various waveform types such as pulsed square waveform, saw-tooth waveform, triangular waveform, and sinusoidal waveform. In an embodiment, the generated drive signal comprises a series of pulses. The coil driver circuit 204 is configured to cooperate with the first signal generator unit 202 to receive the generated drive signal, and is further configured to condition the received signal based on the requirement and number of the treatment coils 206a-s. The coil driver circuit 204 is configured to provide the conditioned drive signal to the treatment coils 206a-s for facilitating generation of the electromagnetic signal. The treatment coils 206a-s are electromagnetic coils. The treatment coils 206a-s may be toroidal, spiral, or helical in shape. The treatment coils 206a-s generate the electromagnetic signal to facilitate treatment of medical condition corresponding to the selected program. The treatment coils 206a-s are spaced such that the electromagnetic wave generated by the treatment coils 206a-s has substantially uniform field strength. In an embodiment, the generated electromagnetic signal is a pulsed electromagnetic signal.

In one embodiment, the waveform generator unit 112 generates the electromagnetic signal for facilitating treatment of medical conditions by improving the zeta potential of cells in the body of the patient. The membrane of a healthy cell is negatively charged inside and has a positive charge outside of the cell. The flow of charges across the cell membrane generates electrical currents. When the body needs to send a message from one point to another, a cell is stimulated. Upon stimulation, the cell allows positive charges to enter through open ion channels. This causes the inside of the cell to become more positively charged, which triggers electrical currents that can turn into electrical pulses. A disruption in these electrical currents can lead to illness. The electromagnetic signal generated by the device 100 facilitates motion of ions and electrolytes in the cells, tissues and fluids within the body. This movement stimulates a vast array of chemical and electric interactions in the cells and tissues of the body, thereby helping them to rebalance. Thus, the disruption of the electrical current is eliminated and the cell is restored. It is well-known that there is direct correlation between voltage of a cell membrane and its pH value. A higher pH value corresponds to an acidic pH. A solution with a higher pH value includes a number of free radicals or electron stealers. A free radical is a molecule that is missing electrons and goes looking for healthy cells to steal electrons. This stealing process destroys or at the very least severely impairs the function of the cell which had the electrons stolen from it. However, an antioxidant is a molecule that is capable of giving away or donating electrons, thus rendering previously volatile, toxic cells harmless. When the pH increases, the cell voltage becomes positive. A high positive cell voltage gives indication of the disease process initiation. Above a certain positive cell voltage values, DNA damage occurs and cancer growth is initiated. The device 100 avoids disease initiation and cell damage by generating electromagnetic signals to restore the healthy voltage across the cell membrane.

In another embodiment, the therapeutic signal is an electrical signal. The waveform generator unit 112 includes a second signal generator unit configured to generate the electrical signal of the pre-determined values of at least one of voltage, current, and frequency associated with the selected program for facilitating treatment of medical condition corresponding to the selected program.

In an embodiment, the device 100 includes both the first signal generator unit 202 and the second signal generator unit.

In an embodiment, the second signal generator unit is connectable to red, near-infrared, and infrared Light Emitting Diodes (LEDs) to enable generation of red, near-infrared, and infrared light beams for facilitating treatment of medical conditions. For example, red light therapy is typically used to treat cosmetic skin issues, like stretch marks and wrinkles. Red light therapy is also used to treat conditions, like psoriasis, slow-healing wounds, and even the side effects of chemotherapy. In another embodiment, the second signal generator unit is connectable to a current control unit to provide electrical stimulation therapies including at least one of facial stimulation, pelvic stimulation, Transcutaneous Electrical Nerve Stimulation (TENS), Interferential Therapy (IFT), Defibrillation, and electro-acupuncture for facilitating treatment of medical conditions. The device 100 may be connectable to a plurality of electrodes for providing electrical stimulation therapies to the patient. The current control unit and the LEDs can also be connected to the first signal generator unit 202 to provide electrical stimulation therapies and red, near-infrared, or infrared therapies.

In an embodiment, the device 100 includes at least one of an HDMI interface and a USB interface for storing a plurality of music notes to facilitate healing of the patient with the help of music therapy. Music therapy is known to improve invasive procedures, restore lost speech, reduce side effects of cancer therapy, and relieve pain. It substantially improves quality of life for dementia patients. In another embodiment, the device 100 is connectable to a thermal pad for facilitating healing of the patient by using thermotherapy. Thermotherapy is beneficial to people with arthritis and stiff muscles and injuries to the deep tissue of the skin. Heat may be an effective self-care treatment for conditions like rheumatoid arthritis. The therapeutic effects of heat include increase in the extensibility of collagen tissues, decrease in joint stiffness, reduction in pain, relieving muscle spasms, reduction in inflammation, edema. Thermotherapy also aids in the post-acute phase of healing and increasing blood flow. The increased blood flow to the affected area provides proteins, nutrients, and oxygen for better healing.

In an embodiment, the input unit 102 includes at least one of a keypad, a touch screen, push buttons, and toggle switches.

Advantageously, the device 100 is embedded with a wireless communication module selected from a group consisting of 2G (GSM), 3G (GPRS), 4G (LTE), narrowband IoT (NB-IoT/5G), Zigbee modules for facilitating wireless communication with a remote cloud server 302. The device 100 facilitates real-time monitoring of the parameters remotely via a monitoring device 300 communicatively coupled to the remote cloud server 302.

In an embodiment, the device 100 includes a health evaluation unit 116 comprising a signal conditioning unit 118 and a comparator 120. The signal conditioning unit 118 is configured to cooperate with the sensors 104a-n to receive the detection signals, and is further configured to generate detection values based on the detection signals. The comparator 120 is configured to cooperate with the signal conditioning unit 118 to receive the detection values, and is further configured to compare each of the received detection values with at least one pre-determined threshold value to evaluate the health condition of the patient. The comparator 120 is configured to generate an alert signal when the detection values become equal to the pre-determined threshold values. In an embodiment, the health evaluation unit 116 is implemented using one or more processors.

In an embodiment, the health evaluation unit 116 is configured to send the generated alert signal to the monitoring device 300 via the remote cloud server 302. The monitoring device 300 receives the alert signal and generates an alert notification to notify a physician or a caretaker about the abnormal health parameters of the patient. With the IoT (Internet of Things) platform, the concerned doctor can monitor the critical as well as routine patients. Advantageously, the device 100 is integrated with a hospital's health record/patient management system via the remote cloud server 302. In an embodiment, a back office can be run to monitor patients round the clock using a robotic automation process.

In another embodiment, the device 100 facilitates provision of the inputs remotely through the monitoring device 300 via the remote cloud server 302. The device 100 may also allow remote upgradation of the programs for each of the medical conditions. The device 100 is programmable to a frequency range of 0.01 Hz to 300 THz, voltage range from 2 V to 80 V, and current range from 5 mA to 5 A.

In yet another embodiment, the cloud server 302 includes a data logger unit and a data analytics unit. The data logger unit is configured to receive the detection values and the selected program (i.e. pre-determined values of at least one of voltage, current, and frequencies selected by the user) corresponding to the detection values from the device 100, and is further configured to create a log of the received detection values and the program. The server 302 may store a log of detection values and the selected programs for a plurality of devices 100 associated with a plurality of patients. The data analytics unit is configured to analyze the logged data of detection values and selected programs, and is further configured to identify a pattern in the logged data to determine a mathematical function relating the logged detection values with the selected programs. The data analytics unit may employ one or more machine learning techniques for determining the mathematical relationship. As the data log is updated continuously, the mathematical function is also regularly/periodically updated to accurately define relationship between the detection values and the selected programs.

In an exemplary embodiment, the server 302 coordinates with the therapeutic devices 100 of multiple patients to receive the detection values, identifies discrepancies or medical conditions and corresponding treatment program to be selected based on the received detection values and the mathematical function, generates corresponding control signals, and sends the control signals to the therapeutic devices 100 for automatic selection of programs to provide treatment to the patients using the devices 100.

In an embodiment, the server 302 sends the mathematical function to the therapeutic devices 100 after every updation. Based on the received mathematical function, the devices 100 update/modify the programs stored in the memory 108 to provide accurate treatment to the patients based on the monitored parameters and identified medical condition. Thus, the device 100 allows automatic upgradation of the programs for each of the medical conditions.

In an embodiment, the device 100 and/or the server 302 may be integrated with the Hospital Health Record system to draw insights from the patient's historic and progressive records captured from time to time. This data can be used to draw the intelligence and recommend the usage pattern of the device 100.

Advantageously, the cloud server 302 may be a quantum cloud server that supports data analytics using quantum computing.

The device 100 includes a power source 114 selected from a group consisting of a battery, a solar panel, and a DC-DC converter unit connectable to an AC power source. In an embodiment, the device 100 includes a radio frequency (RF) receiver antenna and a rectifier. The RF receiver antenna receives RF signals. The rectifier converts the RF signals into DC power. The DC-DC converter converts the DC power into power required for charging the battery.

Advantageously, the device 100 is capable of integrating with the oxygen supply monitoring and regulating system in hospital or individual supply units. The device 100 can also be integrated with portable blood diagnosis systems, portable oxygen machines, acupressure systems, or other such medical devices to allow diagnosis of the illnesses or disorders from the blood line of the patient and automatic running of the program based on the diagnosis.

Advantageously, the device 100 is a portable and wearable device. The device 100 may be customized as per the patient's requirement. It can be designed in the form of a wrist watch, a wrist band, or even a hospital bed.

The device 100 creates vibrations in the body using different forms of energies including electrical, electromagnetic, and mechanical vibrations to treat the patients naturally. In an exemplary embodiment, the sensors 104*a-n* continuously monitor the health of a patient. The parameters being monitored are continuously sent to the control unit 106. The device 100 detects discrepancies/medical conditions from the monitored parameters using the mathematical function. If any discrepancy is found in the parameters, the control unit 106 automatically selects a program to generate an electrical or electromagnetic signal to heal the patient and overcome the discrepancy. The device 100 may not be able to detect certain medical conditions. In that case, the input unit 102 of the device 100 receives a manual input for a program selection from a user. Based on the input, the control unit 106 generates an electrical or electromagnetic signal to heal the patient. The control unit 106 may be configured to receive inputs from both the sensors 104*a-n* and the input unit 102 at the same time and perform the functions of monitoring and healing simultaneously. During monitoring, if an emergency health situation arises, the health evaluation unit 116 generates an alert signal. The alert signal is received at the remote monitoring device 300, which may be a hospital's computer, a physician's, or a caretaker's user device to notify them about the emergency health situation. The doctors or caretakers can then take suitable actions to help the patient during emergency situation. Thus, the device 100 that enables patients to access emergency healthcare.

In another exemplary embodiment, the device 100 is used for monitoring blood glucose level in a diabetic person. When the blood glucose level exceeds a pre-defined value, the device 100 generates a therapeutic signal at a dedicated frequency for controlling the blood glucose level.

The foregoing description of the embodiments has been provided for purposes of illustration and not intended to limit the scope of the present disclosure. Individual components of a particular embodiment are generally not limited to that particular embodiment, but, are interchangeable. Such variations are not to be regarded as a departure from the present disclosure, and all such modifications are considered to be within the scope of the present disclosure.

The present disclosure described herein above has several technical advantages including, but not limited to, the realization of a medical therapeutic device that:
- facilitates real-time monitoring of various health parameters of a patient's body;
- is capable of treating multiple illnesses and disorders;
- restores the zeta potential of the body cell;
- facilitates remote monitoring of patient's health;
- can be integrated with a hospital's health record system;
- is wearable;
- notifies a physician, a registered hospital, or a caretaker about a medical emergency situation;
- enables a patient to access emergency healthcare; and
- is capable of treating blood-related illnesses and disorders.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The use of the expression "at least" or "at least one" suggests the use of one or more elements or ingredients or quantities, as the use may be in the embodiment of the disclosure to achieve one or more of the desired objects or results.

Any discussion of documents, materials, devices, or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A therapeutic device for monitoring and treating medical conditions of patients, said device comprising:

an input unit configured to receive at least one input from a user;

a plurality of sensors configured to monitor a plurality of pre-determined parameters associated with the health of the patient, said sensors further configured to generate detection signals based on said monitored parameters;

a control unit configured to cooperate with said input unit and said sensors, said control unit comprising:
- a memory having a list of medical conditions to be treated and a program corresponding to each of said medical conditions, each of said programs comprising predetermined values of at least one of voltage including positive and negative values, current, frequency and a suggestion of thermotherapy where applicable for treating corresponding medical conditions; and
- a controller configured to receive said input from said input unit and said detection signals from said sensors, said controller further configured to cooperate with said memory to select a program based on said received input, detection signals, or a combination thereof, a waveform generator unit configured to cooperate with said control unit to receive said selected program, and further configured to generate a therapeutic signal including a series of pulses being an electromagnetic or an electric signal of said predetermined value of at least one of voltage including positive and negative voltage values, current, and frequency associated with the selected program for generating said signal for facilitating the treatment of medical conditions by improving a zeta potential of cells in a body of the patient, said waveform generator unit including:
- a plurality of treatment coils for generating said electromagnetic signal to facilitate treatment of medical conditions corresponding to said selected program;
- a first signal generator unit configured to generate a drive signal of said predetermined values of at least two of voltage between +80V and +2V or −2V and −80V, current between 5 mA and 5 A, and frequency between 0.01 Hz and 300 THz, associated with the selected program;
- a coil driver circuit configured to cooperate with said first signal generator unit to receive said generated drive signal, and further configured to condition said received drive signal based on the requirement and number of said treatment coils, said coil driver circuit configured to provide the conditioned first signal to said treatment coils for facilitating generation of said electromagnetic signal; and
- a second signal generator unit configured to generate said electrical signal of said predetermined values of at least two of voltage between +80V and +2V or −2V and −80V, current between 5 mA and 5 A, and frequency between 0.01 Hz and 300 THz, associated with the selected program for facilitating treatment of medical condition corresponding to said selected program;

a coupling means for mounting said waveform generator unit in proximity to the patient's body for injecting the therapeutic signal into the patient's body to facilitate treatment of the medical condition corresponding to said selected program; and a thermal pad connectable to the device for facilitating healing of the patient by using thermotherapy.

2. The device as claimed in claim 1, wherein said sensors include at least one of an Electrocardiogram (ECG) sensor, a photoplethysmogram (PPG) sensor, an electroretinogram (ERG) sensor, a myogram sensor, a blood pressure sensor, a glucometer, a temperature sensor, an oxygen saturation sensor (SpO2 sensor), a heart rate sensor, an Invasive (intra-arterial) blood pressure (IBP) sensor, a heart chamber pressure sensor, a neuromuscular monitoring device, an End-Tidal CO2 sensor (EtCO2 sensor), a pulse oximeter, and a fitness tracker for tracking stress, heart rate variability (HRV), sleep data, steps, calories burnt, cumulative distance walked, and heart activity data of the patient.

3. The device as claimed in claim 1, wherein said waveform generator unit is implemented using a microcontroller.

4. The device as claimed in claim 1, wherein said treatment coils are electromagnetic coils.

5. The device as claimed in claim 1, wherein said input unit includes at least one of a keypad, a touch screen, push buttons, and toggle switches.

6. The device as claimed in claim 1, further comprising red, near-infrared and infrared Light Emitting Diodes (LEDs) connectable to said second signal generator unit to enable generation of red, near-infrared, and infrared light beams for facilitating treatment of medical conditions.

7. The device as claimed in claim 1, wherein said second signal generator unit is connectable to a current control unit to provide electrical stimulation therapies including at least one of facial stimulation, pelvic stimulation, Transcutaneous Electrical Nerve Stimulation (TENS), Interferential Therapy (IFT), Defibrillation, and electro-acupuncture for facilitating treatment of medical conditions.

8. The device as claimed in claim 1, wherein said device is embedded with a wireless communication module selected from a group consisting of 2G (GSM), 3G (GPRS), 4G (LTE), narrowband IoT (NB-IoT/5G), Zigbee modules for facilitating wireless communication with a remote cloud server.

9. The device as claimed in claim 8, wherein said device facilitates real-time monitoring of said parameters remotely via a monitoring device communicatively coupled to said remote cloud server.

10. The device as claimed in claim 8, wherein said device facilitates provision of said inputs remotely through said monitoring device via said remote cloud server.

11. The device as claimed in claim 8, wherein said device is integrated with a hospital's health record system via said remote cloud server.

12. The device as claimed in claim 8, which allows manual or automatic upgradation of said programs remotely via said remote cloud server, wherein said automatic upgradation is performed using machine learning techniques.

13. The device as claimed in claim 1, wherein said device includes a power source selected from a group consisting of a battery, a solar panel, and a DC-DC converter unit connectable to an AC power source.

14. The device as claimed in claim 1, wherein said device includes at least one of an HDMI interface and a USB interface for storing a plurality of music notes to facilitate healing of the patient with the help of music therapy.

15. The device as claimed in claim 1, wherein said monitored parameters include heart rate, pulse rate, ECG, PPG, Blood Pressure (BP), oxygen saturation (SpO2), level of carbon dioxide released at the end of expiration, respiration rate, neuromuscular blockade, blood glucose level, skin temperature, calories burnt, stress level, cumulative distance walked, and duration of sleep.

16. The device as claimed in claim 1, wherein said device includes a health evaluation unit comprising:
- a signal conditioning unit configured to cooperate with said sensors to receive said detection signals, and further configured to generate detection values based on said detection signals; and
- a comparator configured to cooperate with said signal conditioning unit to receive said detection values, and further configured to compare each of said received detection values with at least one predetermined threshold value to evaluate the health condition of the patient, said comparator configured to generate an alert signal when said detection values become equal to said predetermined threshold values.

17. The device as claimed in claim 16, wherein said health evaluation unit is configured to send said generated alert signal to said monitoring device via said remote cloud server.

18. The device as claimed in claim 1, wherein said device is a portable and wearable device.

19. The device as claimed in claim 1, wherein said coupling means is made of a conducting material.

20. The device as claimed in claim 1, where said coupling means is selected from a group consisting of a belt, a contact surface, a set of probes, cables, and a set of electrodes.

* * * * *